United States Patent
Haseyama et al.

(10) Patent No.: US 7,132,495 B2
(45) Date of Patent: Nov. 7, 2006

(54) POLYISOCYANATE COMPOUND, METHOD FOR PRODUCING THE SAME, AND USES THEREOF

(75) Inventors: Ryuji Haseyama, Sodegaura (JP); Isao Fukada, Takaishi (JP); Akira Matsuura, Takaishi (JP); Hiroki Mizutani, Mobara (JP); Seiichi Kobayashi, Omuta (JP)

(73) Assignee: Mitsui Chemicals, Inc., Tokyo (JP)

( * ) Notice: Subject to any disclaimer, the term of this patent is extended or adjusted under 35 U.S.C. 154(b) by 16 days.

(21) Appl. No.: 10/921,890

(22) Filed: Aug. 20, 2004

(65) Prior Publication Data

US 2005/0049430 A1 Mar. 3, 2005

(30) Foreign Application Priority Data

Aug. 27, 2003 (JP) ............................ 2003-302244

(51) Int. Cl.
*C08G 18/75* (2006.01)
(52) U.S. Cl. .................. 528/74; 560/347; 560/355; 351/159
(58) Field of Classification Search ............ 560/347, 560/355; 528/74; 351/159
See application file for complete search history.

(56) References Cited

U.S. PATENT DOCUMENTS

| | | | |
|---|---|---|---|
| 3,148,202 A * | 9/1964 | Cox et al. | .............. 560/354 |
| 3,173,590 A | 3/1965 | Buntin | |
| 3,317,387 A | 5/1967 | Prichard | |
| 3,470,248 A | 9/1969 | Brotherton et al. | |
| 6,207,364 B1 | 3/2001 | Takamuki et al. | |
| 2004/0026658 A1 | 2/2004 | Yoshimura et al. | |

FOREIGN PATENT DOCUMENTS

| | | |
|---|---|---|
| GB | 1026506 | 4/1966 |
| JP | 26219921 B2 | 11/1990 |
| JP | 03-220167 A | 9/1991 |
| JP | 11-140041 A | 5/1999 |
| JP | 2002-082203 | 3/2002 |

OTHER PUBLICATIONS

Ulrich; Chemistry and Technology of Isocyanates; 1996; p. 341.*

* cited by examiner

*Primary Examiner*—Rachel Gorr
(74) *Attorney, Agent, or Firm*—Buchanan Ingersoll & Rooney PC

(57) ABSTRACT

The invention provides an optical material being excellent in balance between the heat resistance, Abbe number and refractive index by providing a compound represented by the general formula (1):

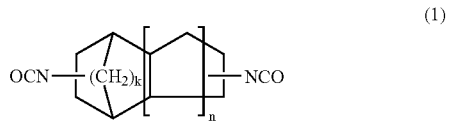

(1)

in the formula, k and n representing integers of 0 to 2 and 0 to 1, respectively, with the proviso that k and n are not simultaneously zero, and k=0 meaning that —$(CH_2)_k$- is not included in the formula.

12 Claims, 4 Drawing Sheets

POLYISOCYANATE COMPOUND, METHOD FOR PRODUCING THE SAME, AND USES THEREOF

BACKGROUND OF THE INVENTION

1. Field of the Invention

The present invention relates to a novel alicyclic polyisocyanate compound and a method for producing the same, and a resin obtained using the compound and an optical material comprising the resin.

2. Description of the Related Art

While polyisocyanate compounds are widely used for producing poly(thio)urethane resins and polyurea resins, many reports have been presented in recent years on the application of the polythiourethane resin to optical materials, particularly to plastic lens materials, by noticing that the features of the polythiourethane resins obtained by polymerization of the polyisocyanate compounds and polythiol compounds have high refractive indices.

For example, the polythiourethane resin obtained by allowing xylylene diisocyanate or bisisocyanatomethyl norbornane to react with 1,2-bis[(2-mercaptoethyl)thio]-3-mercaptopropane is reported to be applied to the plastic lens materials (Japanese Patent No. 2621991).

While the optical material described in this Japanese patent above has a high refractive index and heat resistance, the optical materials, particularly the plastic lens materials, have been required to have a high transparency and refractive index as well as higher Abbe number and heat resistance.

SUMMARY OF THE INVENTION

Accordingly, it is an object of the present invention to provide an optical material having a good balance between the high heat resistance, Abbe number and refractive index.

The inventors of the invention have found, through intensive studies for solving the problems above, that the diisocyanate compound in which the isocyanate groups are directly bonded to an alicyclic group having a specified structure is useful as a material for obtaining a resin excellent in optical characteristics such as transparency and heat resistance.

The present invention provides a compound represented by the general formula (1):

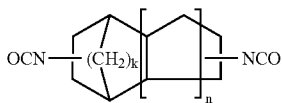

(1)

In the formula, k and n represent integers of 0 to 2 and 0 to 1, respectively, with the proviso that k and n are not simultaneously zero, and k=0 means that —(CH$_2$)k- is not included in the formula.

The compound represented by the general formula (1) may be any one of bicyclo[2.2.1]heptane-2,5(6)-diisocyanate and tricyclo[5.2.1.0$^{2,6}$]decane-3(4),8(9)-diisocyanate.

The present invention also provides a method for producing the alicyclic polyisocyanate compound described above by allowing any one of a compound represented by the general formula (2) and a salt thereof to react with phosgene:

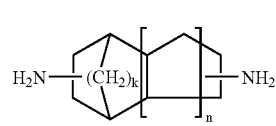

(2)

In the formula, k and n represents integers of 0 to 2 and 0 to 1, respectively, with the proviso that k and n are not simultaneously zero, and k=0 means that —(CH$_2$)k- is not included in the formula.

The present invention also provides a compound represented by the general formula (2):

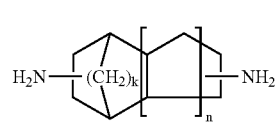

(2)

In the formula, k and n represent integers of 0 to 2 and 0 to 1, respectively, with the proviso that k and n are not simultaneously zero, and k=0 means that —(CH$_2$)k- is not included in the formula.

The present invention also provides a polymerizable composition containing the alicyclic polyisocyanate compound described above.

The present invention also provides a resin. obtained by polymerizing the polymerizable composition described above.

Preferably, the present invention provides an optical material comprising the resin described above, and a lens comprising the optical material described above.

The present invention enables a resin having higher heat resistance to be provided while maintaining a good balance between transparency, refractive index and Abbe number.

The compound represented by the general formula (1) is useful as a material for producing a polyurethane resin, polythiourethane resin, polyurea resin and polyimide resin that are utilized in polymer foams, elastomers, paints, adhesives and films. The resin obtained by using the compound represented by the general formula (1) is suitable as an optical material used for manufacturing optical products such as plastic lenses, filters, recording medium bases and optical fibers.

DESCRIPTION OF THE PREFERRED EMBODIMENTS

Figure 1:
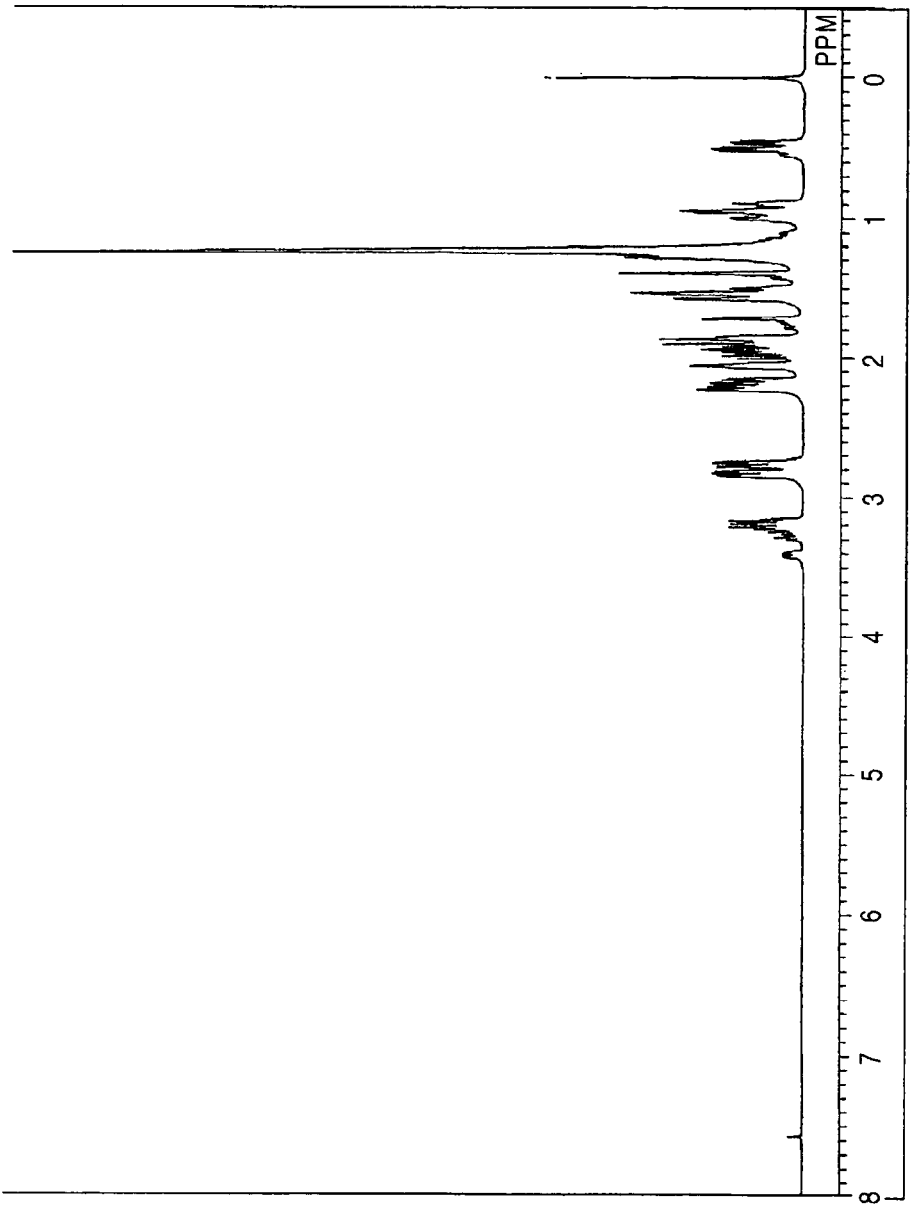
FIG. 1 shows a $^1$H NMR spectrum of bicyclo[2.2.1]-heptane-2,5(6)-diamine.

In formula (1), k and n represent integers of 0 to 2 and 0 to 1, respectively, with the proviso that k and n are not simultaneously zero, and k=0 means that —(CH$_2$)k- is not included in the formula.

Examples of the compound represented by the general formula (1) include bicyclo[4.3.0]nonane-3(4), 7(8)-diisocyanate when k=0 and n=1 in the general formula (1), bicyclo[2.2.1]heptane-2,5(6)-diisocyanate when k=1 and n=0 in the general formula (1), bicyclo[2.2.2]octane-2,5(6)-diisocyanate when k=2 and n=0 in the general formula (1), and tricyclo[5.2.1.0$^{2,6}$]decane-3(4),8(9)-diisocyanate when k=1 and n=1 in the general formula (1).

The expression of bicyclo[4.3.0]nonane-3(4),7(8)-diisocyanate denotes that the compound is a mixture of bicyclo[4.3.0]nonane-3,7-diisocyanate and bicyclo[4.3.0]nonane-4,8-diisocyanate. The compounds similarly described to those above have the same meaning as above.

The compound represented by the general formula (1) is obtained by any one of the following production methods.

In one method, the compound represented by the general formula (1) is produced by synthesizing a corresponding carbamate compound from the compound represented by the general formula (2) and dialkyl carbonate or diaryl carbonate followed by heat decomposition of the carbamate compound. In another method, the compound represented by the general formula (1) is produced by allowing the alicyclic diamine compound represented by the general formula (2) or a salt thereof to react with phosgene. The latter method using phosgene is economically preferable in these two methods.

Examples of the compound represented by the general formula (2) that is used for producing the compound represented by the general formula (1) include bicyclo[4.3.0]nonane-3(4),7(8)-diamine when k=0 and n=1 in the general formula (2), bicyclo[2.2.1]heptane-2,5(6)-diamine when k=1 and n=0 in the general formula (2), bicyclo[2.2.2]octane-2,5(6)-diamine when k=2 and n=0 in the general formula (2), and tricyclo[5.2.1.0$^{2,6}$]decane-3(4),8(9)-diamine when k=1 and n=1 in the general formula (2).

The methods using phosgene include; (A) allowing the compound represented by the general formula (2) to directly react with phosgene, and (B) synthesizing a salt, in advance, such as a hydrochloride salt of the alicyclic diamine compound represented by the general formula (2) followed by allowing the salt to react with phosgene after suspending the salt in an inert solvent.

Method (A) is called as a "cold-and-hot two stage phosgenation method", which comprises a "cold phosgenation reaction" mainly consisting of a reaction for forming carbamyl chloride and an amine hydrochloride (first-stage reaction), and a "hot phosgenation reaction" mainly consisting of heat decomposition of carbamyl chloride to isocyanate and phosgenation of the amine hydrochloride to isocyanate (second-stage reaction).

A solvent is usually used in the reaction between the compound represented by the general formula (2) and phosgene. The solvent is not restricted so long as it does not inhibit the phosgenation reaction. Examples of such solvents include aromatic hydrocarbons such as benzene, toluene, xylene and ethylbenzene; fatty acid esters such as ethyl acetate, butyl acetate and amyl acetate; aromatic carboxylic acid esters such as methyl salicylate, dimethyl phthalate, dibutyl phthalate and methyl benzoate; chlorinated aromatic hydrocarbons such as monochlorobenzene, o-dichlorobenzene and trichlorobenzene; and chlorinated hydrocarbons such as chloroform and carbon tetrachloride. These solvents may be used alone, or as a mixture of at least two of them.

The solvent is usually used in a weight ratio of 4 to 30, preferably 5 to 20, relative to the compound represented by the general formula (2) considering operability and efficiency.

In an example of the preferable embodiment of method (A), the solvent is injected into a reactor, and the reaction system is kept at a pressure of an atmospheric pressure to 1.0 MPa, preferably at a pressure of an atmospheric pressure to 0.5 MPa, and at a temperature of 0 to 80° C., preferably 0 to 60° C. Then, after introducing phosgene 1 to 10 times, preferably 1 to 6 times, in excess to the stoichiometric quantity of the compound represented by the general formula (2), the compound represented by the general formula (2) is dissolved in the solvent and is added to the reaction system. The temperature of the reaction solution is kept in the range of 0 to 80° C., preferably in the range of 0 to 60° C., during the addition, and emitted hydrogen chloride is released out of the reaction system through a reflux condenser. The content of the reactor is a slurry in this stage (cold phosgenation reaction).

Subsequently, the pressure in the reactor is controlled at an atmospheric pressure to 1.0 MPa, preferably 0.05 to 0.5 MPa, and the reaction temperature is raised in the range of 80 to 180° C. in 30 minutes to 5 hours. After increasing the temperature, the reaction is allowed to continue for 30 minutes to 8 hours until the completion of the reaction when the slurry is completely dissolved. Phosgene is appropriately replenished until a sufficient quantity of phosgene is confirmed to be refluxed from the reflux condenser, since dissolved phosgene is vaporized in the temperature increase period and during the high temperature reaction, and is released out of the reaction system through the reflux condenser. After completing the hot phosgenation reaction, the reaction system is purged with an inert gas such as nitrogen gas in the temperature range of 80° C. to 180° C. to purge dissolved excess phosgene and hydrogen chloride (hot phosgenation reaction).

The reaction temperature of the hot phosgenation reaction is usually in the range of 80 to 180° C., preferably in the range of 90 to 160° C. The reaction temperature of 80 to 180° C. is efficient since the reaction rate becomes appropriate without causing any undesirable side reactions.

While the reaction pressure of the hot phosgenation reaction is not particularly restricted, it may be usually selected in the range of an atmospheric pressure to 1.0 MPa from the viewpoint of operability. The preferable reaction pressure is in the range of 0.05 to 0.5 MPa. The reaction system is cooled after completing the reaction, and the compound represented by the general formula (1) is obtained by evaporating the solvent off under a reduced pressure.

The hydrochloride salt of the compound represented by the general formula (2) obtained by method (B) is readily synthesized by treating the compound represented by the general formula (2) with hydrogen chloride or conc. hydrochloric acid.

An example of the embodiment of method (B) is as follows. The sufficiently dried and pulverized hydrochloride of the alicyclic diamine compound is formed into a slurry by dispersing the amine salt in a solvent by strong stirring in a reactor equipped with the same devices as used in the "cold-and-hot two stage phosgenation method" described above. Then, the reaction temperature is kept at 80 to 180° C., preferably at 90 to 160° C., and the reaction pressure is kept at an atmospheric pressure to 1.0 MPa, preferably at 0.05 to 0.5 MPa. Phosgene is introduced into the reactor so that the amount of feed of phosgene is 1 to 10 times of the stoichiometric quantity of phosgene to produce the compound represented by the general formula (1).

The end point of the phosgenation reaction may be presumed by measuring the amount of hydrogen chloride gas generated by the reaction, or by observing that the slurry in the reaction mixture has disappeared. Emitted hydrogen chloride is released out of the reaction system through the reflux condenser. Excess phosgene and hydrogen chloride dissolved in the reaction mixture is purged after completing the reaction. The compound represented by the general formula (1) is obtained by evaporating the solvent off under a reduced pressure after cooling.

The compound represented by the general formula (2) is produced, for example, by converting a dicarbonitrile compound into a corresponding dicarboamide compound by hydrolysis, followed by a Hoffman reaction of the dicarboamide compound, wherein the dicarbonitrile compound is obtained by a reaction of the compound represented by the following general formula (3) with hydrogen cyanide:

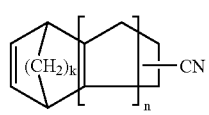

(3)

in the formula, k and n represents integers of 0 to 2 and 0 to 1, respectively, with the proviso that k and n are not simultaneously zero, and k=0 means that —(CH$_2$)k- is not included in the formula.

The polymerizable composition of the present invention contains the compound represented by the general formula (1). An active hydrogen compound having at least two functional groups that react with the isocyanate compound in the molecule may be further contained in the polymerizable composition of the present invention.

While the active hydrogen compound having at least two functional groups that react with the isocyanate compound in the molecule is not particularly restricted, examples of them include polyol, polythiol or mercapto compound having hydroxyl groups, polyamines and polycarboxylic acids. These active hydrogen compounds may be used alone, or as a mixture of at least two of them.

The polyol, polythiol or mercapto compound having hydroxyl group are preferable for use in the optical material among these active hydrogen compounds.

Examples of the polyol, polythiol or mercapto compound having hydroxyl groups include aliphatic hydrocarbon compounds, alicyclic hydrocarbon compounds, aromatic hydrocarbon compounds, and compounds in which a part of carbon atoms are substituted with heteroatoms and in which at least two hydrogen atoms are substituted with hydroxyl groups and/or mercapto groups.

Examples of the compounds in which at least two hydrogen atoms in the aliphatic hydrocarbon compound are substituted with the hydroxyl and/or mercapto group include ethyleneglycol, sorbitol, methanedithiol and 2-mercaptoethanol; examples of the compound in which at least two hydrogen atoms in the alicyclic hydrocarbon compound are substituted with the hydroxyl and/or mercapto group include inositol, bicyclo[4.3.0]-nonanedimethanol and 1-hydroxy-4-mercaptocyclohexane; examples of the compound in which at least two hydrogen atoms in the aromatic hydrocarbon compound are substituted with the hydroxyl and/or mercapto group include dihydroxybenzene, biphenyltetraol, bisphenol A and 1,2-dimercaptobenzene; and examples of the compound in which at least two hydrogen atoms in the compound, in which a part of the carbon atoms of the aliphatic hydrocarbon compounds, alicyclic hydrocarbon compounds and aromatic hydrocarbon compounds are substituted with heteroatoms, are substituted with the hydroxyl and/or mercapto group include tris(2-hydroxyethyl)isocyanurate, 1,2-bis[(2-mercaptoethyl)thio]-3-mercaptopropane and 1-hydroxyethylthio-3-mercaptoethyl thiobenzene.

Examples of the polyamine and polycarboxylic acid include diamines represented by the general formula (2) and dicarboxylic acids obtained by hydrolysis of a hydrogen cyanide adduct (dicyano compound) of the compound represented by the general formula (3).

Polythiols having a high sulfur content are preferable among the active hydrogen compounds for obtaining a high refractive index resin, and 1,2-bis[(2-mercaptoethyl)thio]-3-mercaptopropane is particularly preferable.

The resin of the present invention is obtained by polymerization of the polymerizable composition of the invention.

Polyisocyanate resins are obtained by polymerization of the compound represented by the general formula (1), and polycarbodiimide resins are obtained by decarboxylation polymerization of the compound represented by the general formula (1). Poly(thio)urethane resins are obtained by polymerization of the compound represented by the general formula (1) and at least one active hydrogen compound selected from the polyol, poluthiol or mercapto compound having hydroxyl groups. Polyurea resins and polyimide resins are obtained, respectively, by using the polyamine and polycarboxylic acid as the active hydrogen compounds.

The proportion of use of the compound represented by the general formula (1) and the active hydrogen compound is usually in the range of 0.5 to 3.0, preferably 0.5 to 1.5, in the molar ratio of the isocyanate group/active hydrogen group (functional group), when the polymerizable composition contains the active hydrogen compound.

While a polythiourethane resin is obtained when only polythiol is used as the active hydrogen compound, urethane bonds, allophanate bonds, thiourea bonds and biuret bonds may be partly contained in the resin in addition to the thiourethane bond depending on the object.

For example, it is possible to permit an isocyanato group to further react with a thiocabamic acid S-alkylester bond, or to increase the cross-link density by allowing the isocyanato group to further react with a dithiourethane bond. The reaction temperature should be at least 100° C. higher, and the proportion of the isocyanate component or isothiocyanate component should be higher than the theoretical molar ratio against the active hydrogen compound. The urea bonds and biuret bond may be integrated into the resin using an amine together as a part of the active hydrogen compound. However, attention should be paid on coloring by taking air oxidation into consideration when the isocyanate compound and isothiocyanate compound are handled.

Various substances such as an inner release agent, a chain elongation agent, a cross-linking agent, a light-stabilizing agent, an antioxidant, an oil-soluble dye and a filler may be added, if necessary, to the polymerizable composition of the present invention.

Known reaction catalysts may be appropriately added in order to control the polymerization reaction rate. The preferably used catalyst is a catalyst known as a catalyst for producing polyurethane.

The lens of the present invention is usually manufactured by injection molding. Specifically, the compound represented by the general formula (1), the active hydrogen compound (preferably polythiol) and various additives, if necessary, are mixed; the liquid mixture is degassed by an appropriate method, if necessary; and the mixture is polymerized thereafter by injecting into a mold. The mold may be treated with a known release agent in order to facilitate release of the resin from the mold after the polymerization.

While the polymerization condition cannot be restricted since it largely differs depending on the kind of the monomer used, the kinds and amounts of the additives and the shape of the mold, the temperature range is usually 0 to 180° C. by gradually increasing the temperature from a low temperature to a high temperature in 1 to 100 hours.

The resin of the present invention is colorless and transparent, and has a high refractive index while being excellent in heat resistance and weather resistance. Accordingly, the resin is favorable as a material of a plastic lens, filter, recording medium substrate and optical fiber.

The poly(thio)urethane resin obtained by allowing the compound represented by the general formula (1) to react with at least one active hydrogen compound selected from polyol, polythiol and a mercapto compound having hydroxyl groups is particularly favorable among the resins of the present invention as optical materials for plastic lenses and the like.

The resin of the present invention can be also used as materials for glazing materials, paints and adhesives.

The resin of the present invention may be subjected to physical or chemical treatments such as surface grinding, antistatic treatment, hard-coat treatment, anti-reflection treatment, dying and dimming treatment, if necessary, in order to improve such properties as anti-reflection, hardness, wear resistance, chemical resistance, fog resistance and fashionability.

While the present invention is described in detail with reference to examples and comparative examples, the present invention is by no means restricted to these examples. The gas chromatographic analysis was preformed using a FID as a detector, a 3 m column packed with Uniport-HP 60/80 mesh coated with 10% Silicone OV-17, and nitrogen as a carrier gas.

In the lens performance tests, the refractive index, Abbe number, weather resistance and heat resistance of were evaluated by the following test methods.

The refractive index and the Abbe number was measured at 20° C. using a Pulfrich refractometer.

Weather resistance: The lens resin was attached in a weatherometer equipped with a sunshine carbon arc lamp, and the lens was taken out after a time lapse of 20 hours. The hue of the lens was compared with the hue before the test.

No yellowish change, slight yellowish change and severe yellowish change were evaluated as "excellent", "good" and "poor", respectively.

Appearance: The appearance was evaluated by the naked eye.

Heat resistance: The tip of a needle (0.5 mm in diameter) of a thermo-mechanical analyzer (TAS 300 manufactured by Rigaku Co.) was penetrated into the sample under a load of 50 g, and the heat-deformation initiation temperature was measured by heating the needle at a heating rate of 10° C./min.

EXAMPLE 1

Synthesis of
bicyclo[2.2.1]heptane-2,5(6)-dicarboamide

Added in a 500 mL glass round bottom flask equipped with a stirrer and thermometer were 73.0 g (0.5 mol) of bicyclo[2.2.1]heptane-2,5(6)-dicarbonitrile (manufactured by Mitsui Chemical Co.) and 500 g of 90% sulfuric acid, and the mixture was stirred at 40° C. for 2 hours.

The reaction solution was cooled at room temperature after completing the reaction, and 2 L of ice-water was slowly poured into the solution. A white solid was precipitated by neutralizing the solution with 30% aqueous sodium hydroxide solution while the solution was sufficiently cooled. The precipitated solid was separated by vacuum-filtration using a filter paper, washed with water and dried (yield 48.3 g). A mass-spectroscopic analysis of the solid obtained showed that the compound is bicyclo[2.2.1]heptane-2,5(6)-dicarboamide (EI m/z 182 ($M^+$)). The purity was revealed to be 99% by a gas chromatographic analysis (the yield from bicyclo[2.2.1]heptane-2,5(6)-dicarbonitrile was 53%).

Synthesis of bicyclo[2.2.1]heptane-2,5(6)-diamine

Added into a 2 L glass round bottom flask equipped with a stirrer, thermometer and reflux condenser were 91.1 g (0.50 mol) of bicyclo[2.2.1]heptane-2,5(6)-dicarboamide and 1000 g (2.50 mol) of a 10% aqueous sodium hydroxide solution, and the mixture was cooled at 10 to 15° C. Then, 780 g (1.10 mol) of a 5% aqueous sodium hypochlorite was dripped into the suspension with stirring in 30 minutes so that the temperature does not exceed 15° C. The temperature of the suspension was kept at 10 to 15° C. for 3 hours after completing dripping, and the temperature was increased to room temperature thereafter. After stirring the solution at room temperature for 10 hours, the temperature was increased to 70 to 80° C. with additional stirring for 2 hours.

The reaction solution was cooled at room temperature after completing the reaction, and the residual solid was filtered off by vacuum filtration using a filter paper. The solid was thoroughly dried (dry weight 7.7 g), and was revealed to be unreacted bicyclo[2.2.1]heptane-2,5(6)-dicarboamide from an analysis by IR absorption spectrometry.

Water was evaporated off in vacuum from the filtered solution (1890 g) obtained above. Although solids were precipitated with the advance of concentration, they were intermittently removed by filtration. The residual solution was distilled in vacuum after removing most of water to obtain 42.0 g of a colorless transparent liquid. This liquid was revealed to be bicyclo[2.2.1]heptane-2,5(6)-diamine from the mass spectroscopic analysis (EI m/z 126(M+)). A gas chromatographic analysis showed that the purity is 99% (the yield against bicyclo[2.2.1]heptane-2,5(6)-dicarboamide used was 67%). The $^1$H NMR spectrum of bicyclo[2.2.1]heptane-2,5(6)-diamine is shown in FIG. 1.

Synthesis of
bicyclo[2.2.1]heptane-2,5(6)-diisocyanate

The compound was synthesized by the cold-hot two stage phosgenation method using bicyclo[2.2.1]heptane-2,5(6)-diamine as a starting material. Added in a 10 L pressurizing reactor with a jacket equipped with a electromagnetic induction stirrer, automatic pressure control valve, thermometer, nitrogen inlet line, phosgene inlet line, condenser and material feed pump was 2,500 g of o-dichlorobenzene. Then, 1,425 g (14.2 mol) of phosgene was added through the phosgene inlet line with stirring. Cold water was flowed through the jacket to maintain the inner temperature at about 5° C. A solution prepared by dissolving 302.9 g (2.4 mol) of the diamine compound in 2,500 g of o-dichlorobenzene was fed into the solution above for cold phosgenation at 5 to 10°

C. under an atmospheric pressure in 60 minutes. After completing phosgene to feed, a pale-brown slurry was formed in the flask.

Figure 2:
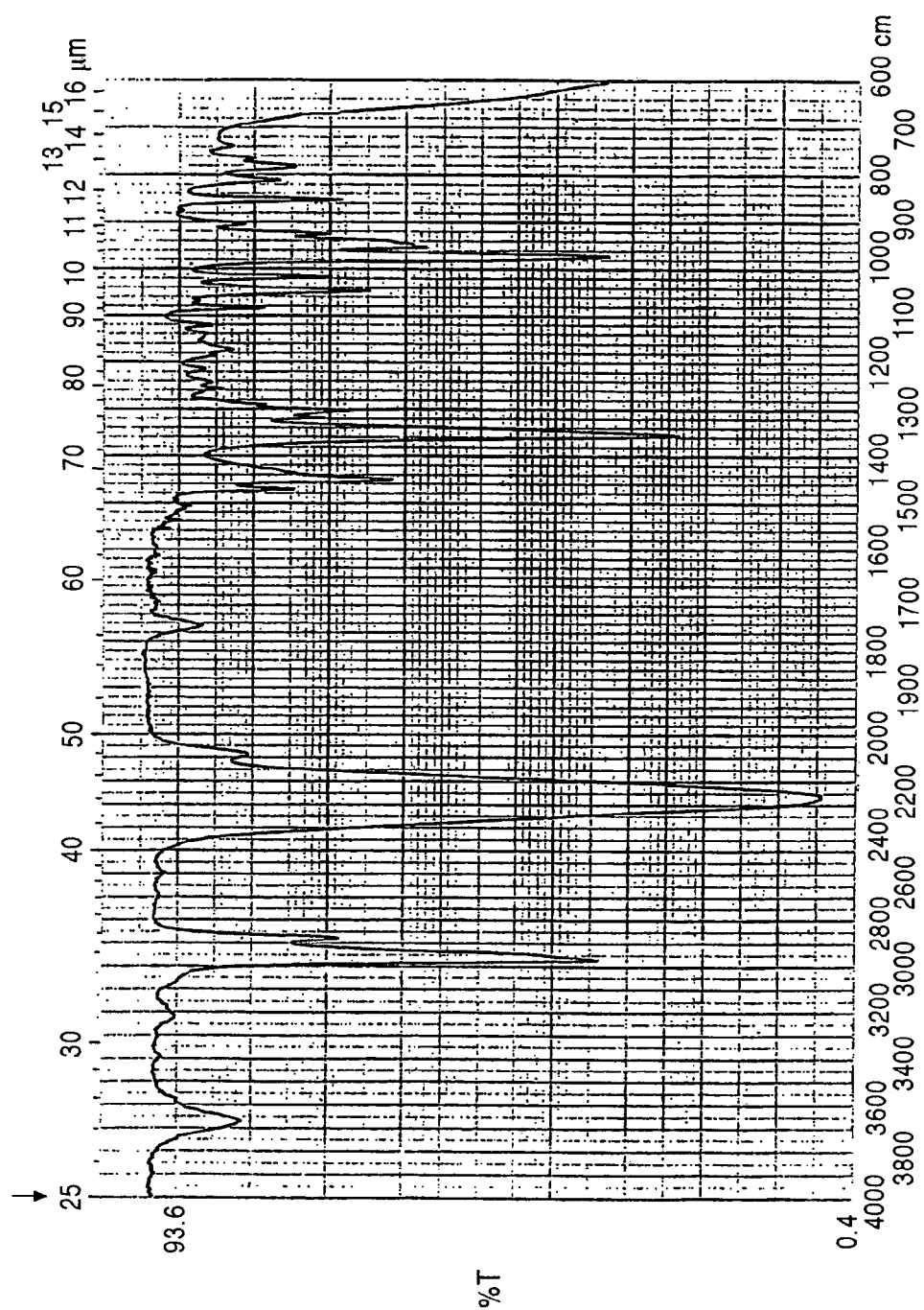
FIG. 2 shows an IR spectrum of bicyclo[2.2.1]-heptane-2,5(6)-diisocyanate.
Figure 3:
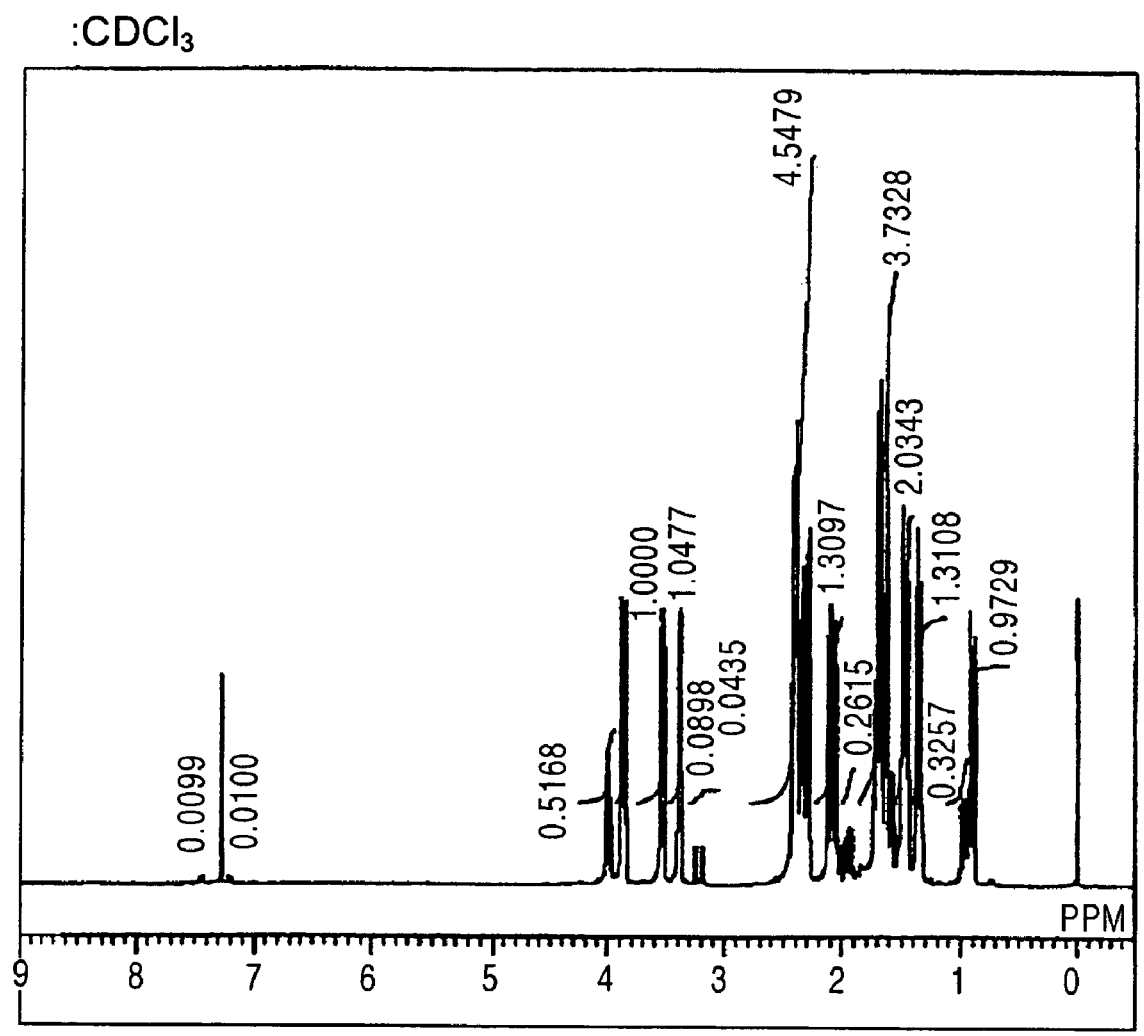
FIG. 3 shows a $^1$H NMR spectrum of bicyclo[2.2.1]-heptane-2,5(6)-diisocyanate.
Figure 4:
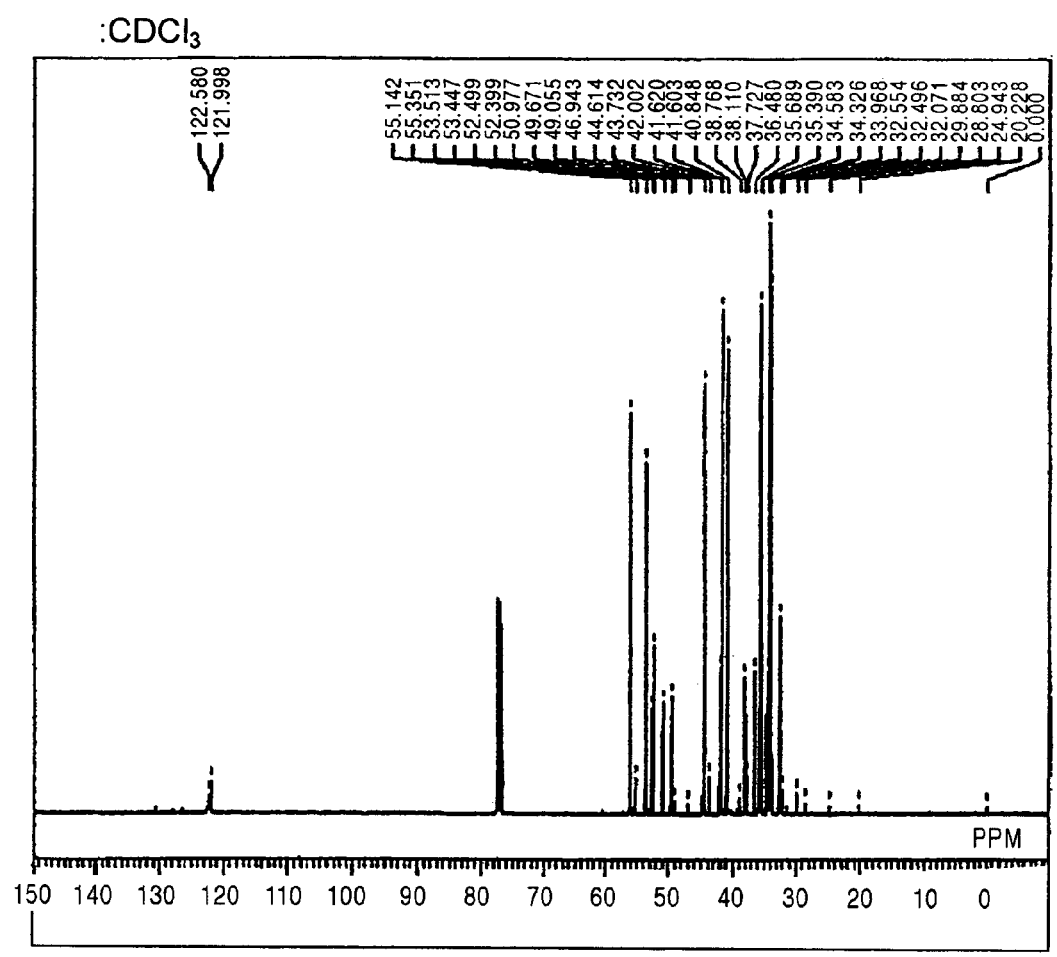
FIG. 4 shows a $^{13}$C NMR spectrum of bicyclo[2.2.1]-heptane-2,5(6)-diisocyanate.

Subsequently, the inside of the reactor was pressurized at 0.2 MPa while the temperature was increased to 150° C. in 60 minutes, followed by hot-phosgenation under a pressure of 0.2 MPa at a reaction temperature of 150° C. for 2 hours. Phosgene (480 g) was replenished during the hot-phosgenation reaction. The liquid in the flask was turned into a pale-brown transparent liquid during the hot-phosgenation reaction. After completing the hot-phosgenation reaction, nitrogen gas was purged at 100 to 150° C. with a flow rate of 100 L/hour for degassing.

o-dichlorobenzene as a solvent was evaporated off under a reduced pressure, and 337 g (yield 79.0%) of a fraction was obtained at a boiling point of 120 to 126° C./0.5 Kpa as a colorless transparent liquid (NCO content 47.0%). The IR spectrum, $^1$H NMR spectrum and $^{13}$C NMR spectrum of the diisocyanate compound thus obtained are shown in FIGS. 2, 3 and 4, respectively.

EXAMPLE 2

Manufacture of Polyurethane Plastic Lens

After forming a homogeneous liquid by mixing 17.8 g (0.1 mol) of bicyclo[2.2.1]heptane-2,5(6)-diisocyanate synthesized in Example 1 and 17.2 g (0.066 mol) of 1,2-bis[(2-mercaptoethyl)thio]-3-mercaptopropane, the liquid was injected into a lens mold comprising a glass mold and gasket, followed by polymerization with heating. The resin thus obtained was colorless and transparent, and was excellent in shock resistance. The refractive index [ne] was 1.636, Abbe number [ve] was 36.9, and the deformation initiation temperature was 167° C. The data are shown in Table 1.

Dibutyltin chloride (1000 ppm) as a catalyst, a UV absorbing agent (500 ppm) and an inner release agent (Zelec UN, 1200 ppm) were used in the polymerization process. The heating pattern for polymerization was a temperature increase up to 120° C. in 20 hours, and a constant temperature of 120° C. for 4 hours and 130° C. for 4 hours.

Comparative Example 1

The resin was prepared by the same method as in Example 2, except that the diisocyanate compound in Example 2 was changed to 18.8 g (0.1 mol) of 1,3-bisisocyanatomethyl cyclohexane.

Comparative Example 2

The resin was prepared by the same method as in Example 1, except that the diisocyanate compound in Example 1 was changed to 20.7 g (0.1 mol) of bisisocyanatomethylnorbornane. The data of optical properties of the resins obtained are shown in Table 2.

TABLE 1

| EVALUATION OF PLASTIC LENS | REFRACTIVE INDEX ne | ABBE NUMBER ve | HEAT DEFORMATION INITIATION TEMPERATURE Tg (° C.) |
|---|---|---|---|
| EXAMPLE 1 | 1.636 | 36.9 | 167 |
| COMPARATIVE EXAMPLE 1 | 1.618 | 37.9 | 102.6 |

TABLE 1-continued

| EVALUATION OF PLASTIC LENS | REFRACTIVE INDEX ne | ABBE NUMBER ve | HEAT DEFORMATION INITIATION TEMPERATURE Tg (° C.) |
|---|---|---|---|
| COMPARATIVE EXAMPLE 2 | 1.619 | 39.0 | 109 |

The results of the weather resistance tests were all excellent.

What is claimed is:

1. A compound selected from the group consisting of bicyclo[2.2.1]heptane-2,5(6)-diisocyanate, tricyclo[5.2.1.0$^{2,6}$]decane-3(4),8(9)-diisocyanate, bicyclo[4.3.0]nonane-3(4),7(8)-diisocyanate and bicyclo[2.2.2]octane-2,5(6)-diisocyanate.

2. The compound according to claim 1, wherein the compound is any one of bicyclo[2.2.1]heptane-2,5(6)-diisocyanate and tricyclo[5.2.1.0$^{2,6}$]decane-3(4),8(9)-diisocyanate.

3. A method for producing the compound according to claim 2 comprising the step of allowing any one of the compounds represented by bicyclo[2.2.1]heptane-2,5(6)-diamine, tricyclo[5.2.1.0$^{2,6}$]decane-3(4),8(9)-diamine and a salt thereof to react with phosgene.

4. A polymerizable composition containing the compound represented by the general formula (1) according claim 1.

5. A polymerizable composition according to claim 4 containing at least one active hydrogen compound selected from mercapto compounds having polyol, polythiol and hydroxyl groups.

6. A resin obtained by polymerization of the polymerizable composition according to claim 5.

7. An optical material comprising the resin according to claim 6.

8. A lens comprising the optical material according to claim 7.

9. A method for producing the compound according to claim 1 comprising the step of allowing any one of the compounds represented by the general formulae (2) and a salt thereof to react with phosgene:

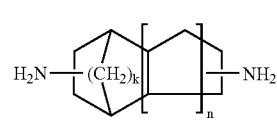

(2)

in the formula, k and n representing integers of 0 to 2 and 0 to 1, respectively, with the proviso that when the compound is bicyclo[2.2.1]heptane-2.5(6)-diisocyanate, k=1 and n=0; when the compound is tricyclo[5.2.1.0$^{2,6}$]decane-3(4),8(9)-diisocyanate, k=1 and n=1; when the compound is bicyclo[4.3.0]nonane-3(4),7(8)-diisocyanate, k=0 and n=1; and when the compound is bicyclo[2.2.2]octane-2,5(6)-diisocyanate, k=2 and n=0.

10. A resin obtained by polymerization of the polymerizable composition according to claim 4.

11. An optical material comprising the resin according to claim 10.

12. A lens comprising the optical material according to claim 11.

* * * * *